Figure 1:
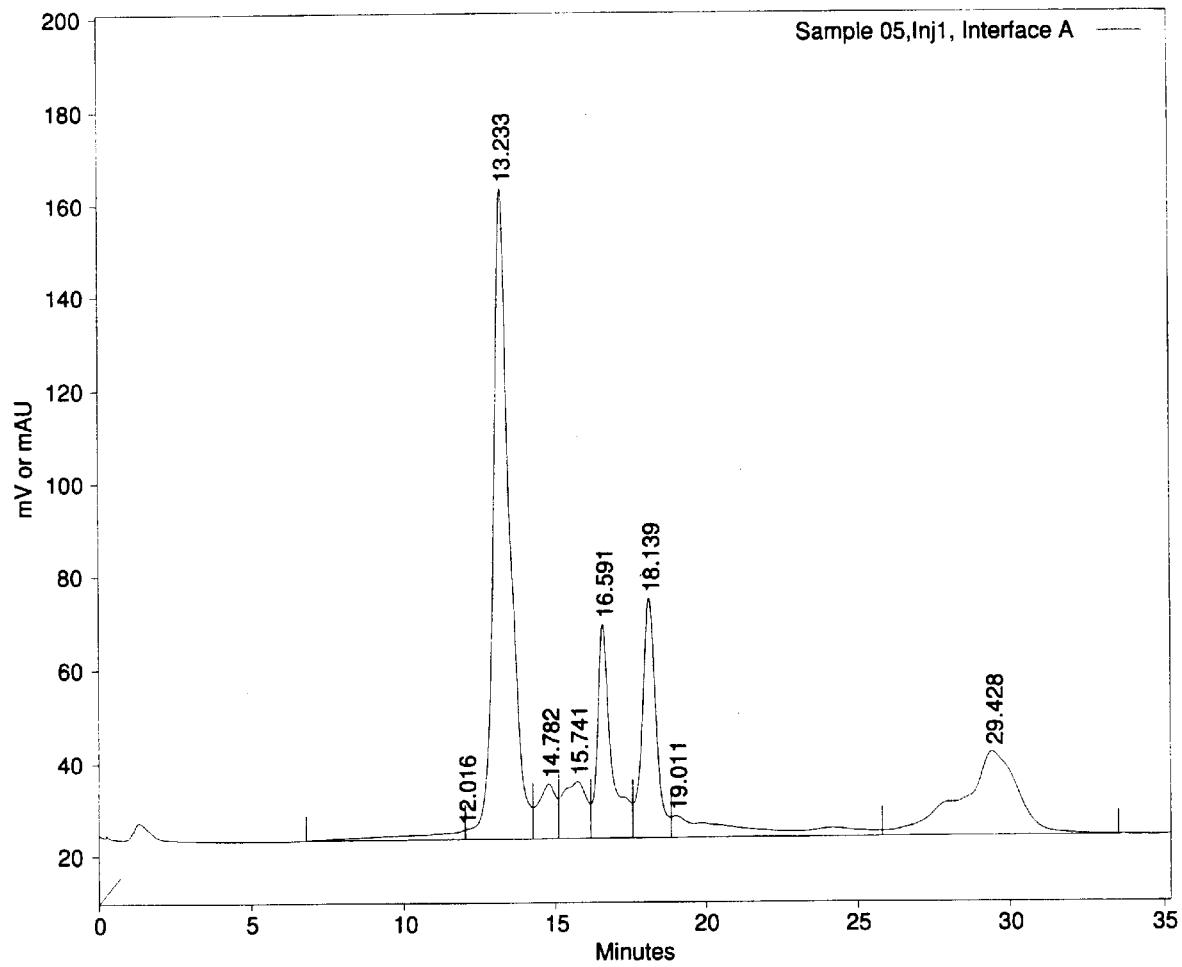

United States Patent [19]
Kussendrager et al.

[11] Patent Number: 6,010,698
[45] Date of Patent: Jan. 4, 2000

[54] PROCESS FOR RECOVERING GROWTH FACTORS, OR A COMPOSITION CONTAINING ONE OR MORE GROWTH FACTORS, FROM MILK OR A MILK DERIVATIVE

[75] Inventors: Klaas Daniël Kussendrager, Veghel; Marinus Gerardus Cornelis Kivits, Schijndel; Hubert Karel Lemmen, Handel; Theodorus Johannes Antonia Maria van Kessel, Vorstenbosch, all of Netherlands

[73] Assignee: Campina Melkunie B. V., Netherlands

[21] Appl. No.: 09/046,821

[22] Filed: Mar. 24, 1998

[30] Foreign Application Priority Data

Mar. 27, 1997 [NL] Netherlands .......................... 1005677

[51] Int. Cl.⁷ .......................... A61K 38/43; A61K 38/00; C07K 5/00; C07K 7/00
[52] U.S. Cl. ........................... 424/94.1; 514/12; 530/324
[58] Field of Search ............................. 424/94.1; 514/12; 530/324

[56] References Cited

FOREIGN PATENT DOCUMENTS

| 9200994 | 1/1992 | WIPO . |
| 9313676 | 7/1993 | WIPO .............................. A23J 1/20 |
| 9509933 | 11/1995 | WIPO . |
| 9529933 | 11/1995 | WIPO .............................. C07K 1/18 |

OTHER PUBLICATIONS

Francis, *J. Dairy Sci.*, 78, pp. 1209–1218 1995.

*Primary Examiner*—Avis M. Davenport
*Attorney, Agent, or Firm*—Cooper & Dunham LLP; Robert D. Katz, Esq.

[57] ABSTRACT

The invention relates to a process for recovering one or more growth factors from milk or a milk derivative, comprising adsorbing at least one growth factor from the milk or the milk derivative to a cation exchanger, followed by fractionated elution of the cation exchanger, whereby at least one fraction is obtained which is enriched in growth factors, followed by the further treatment of this fraction at a pH of at least 3.5 and not more than 4.5.

24 Claims, 4 Drawing Sheets

PROCESS FOR RECOVERING GROWTH FACTORS, OR A COMPOSITION CONTAINING ONE OR MORE GROWTH FACTORS, FROM MILK OR A MILK DERIVATIVE

This invention relates to a process for recovering growth factors, or a composition containing one or more growth factors, from milk or a milk derivative.

Milk contains, in addition to the so-called macronutrients (fats, proteins, carbohydrates), a large number of microcomponents with a specific functionality. The most well-known among them are lactoferrin and lactoperoxidase, but a variety of growth factors also belong to this group of microcomponents.

Lactoferrin and lactoperoxidase can be eminently recovered from milk or milk products on an industrial scale. U.S. Pat. No. 5,596,082 discloses a process in which lactoferrin and lactoperoxidase are adsorbed to a cation exchanger by passing milk or a milk product at a high superficial velocity (more than 500 cm per hour) and at a high liquid load (100–600 bed volumes per hour) over the cation exchanger and then eluting the cation exchanger with a number of salt solutions of different concentrations. Thus a lactoferrin-containing fraction and a lactoperoxidase-containing fraction are obtained, which can be further treated in a conventional manner.

The growth factors present in milk and milk derivatives have different, highly specific activities. These activities, the nature of which is often indicated by the name of the growth factor in question, can have positive effects in humans. It has been suggested to use Epidermal Growth Factor (EGF) to promote skin recovery in wounds. Insulin Growth Factor (IGF) is assumed to play an important role in bone formation metabolism. Angiogenin, too, which is supposed to induce blood vessel growth, is considered to belong to the group of growth factors.

Reviews of the growth factors present in milk are given by inter alios D. Schams in Endocrine Regulations, 28, (1994), 3–8 and by C. E. Grosvenor et al. in Endocrine Reviews, 14, (1992), 710–728. This last article further gives a qualitative review of the hormones present in milk.

In the prior art, different methods are described for isolating other microcomponents than lactoferrin and lactoperoxidase from milk.

European patent application 0 556 083 discloses a process in which a so-called "secretory component" is isolated. According to this process, milk or a milk derivative is adsorbed to a cation exchanger, whereafter different fractions are obtained by elution with salt solutions of different concentrations. In addition to a fraction which contains the "secretory component", lactoferrin- and lactoperoxidase-containing fractions are thereby obtained. However, owing to the long contact times required in the adsorption and the low rates of throughput that can be realized, this process is not suitable for industrial application.

WO-A-95/26984 discloses a process for preparing a composition containing a bovine insulin-like growth factor-1, starting from pre-heated cheese whey or skim milk. The type and the amount of the growth factors that can be isolated, however, are limited in this process.

European patent application 0 489 884 discloses the isolation of growth factors from colostrum, a raw material naturally rich in growth factors. The process described requires a number of successive chromatographic steps with different column packings. According to this process, it appears that only half of the growth factors present can be recovered.

WO-A 9529933 discloses the isolation of acid-modified growth factors at a pH of 2 to 3. In this process, desired, but especially also undesired modifications can occur.

It is an object of the invention to provide a process for recovering one or more growth factors from milk or milk derivatives, in which a high yield of growth factors can be realized.

It is another object of the invention to provide a process for recovering one or more growth factors from milk or milk derivatives, which can be combined with an industrial process for recovering lactoferrin and lactoperoxidase, and without the recovery of the growth factor(s) having any appreciable adverse effect on the yield of lactoferrin and lactoperoxidase vice versa.

A possible way of achieving these objects could consist in adsorbing the growth factors from the milk or the milk derivative onto a cation exchanger, followed by fractionated elution of the cation exchanger. It has presently been found, however, that the further treatment of a thus obtained fraction enriched in growth factors presents problems.

A fraction obtained after adsorption to a cation exchanger followed by elution is normally subjected to a few subsequent treatments, such as desalting, concentration, removing and/or killing off bacteria present, and drying. It has been found, on the one hand, that in the practice of these treatments unacceptably large amounts of growth factors are lost, and, on the other hand, that the equipment required in the practice of the treatments mentioned, such as filters and ion exchangers, already requires cleaning and/or replacement after it has been used for only a short time.

Accordingly, a further object of the invention is to provide a process for recovering one or more growth factors from milk or milk derivatives, in which the further treatment of a growth factor-enriched fraction hardly, if at all, affects the yield of growth factors.

A still further object of the invention is to isolate growth factors in the form in which they are naturally present in milk, while no modification, or substantially no modification, of the growth factors occurs.

The invention is based on the surprising insight that these and other objects can be achieved by carrying out the further treatment under mildly acid conditions at a pH greater than 3.0.

According to the invention, the above objects can be achieved without the problems mentioned occurring in the further treatment, in that at least one growth factor is adsorbed from the milk or the milk derivative to a cation exchanger, followed by fractionated elution of the cation exchanger, whereby at least one fraction is obtained which is enriched in growth factors, followed by the further treatment of this fraction at a pH of at least 3.5 and not more than 4.5.

It has presently been found that when the treatment of the growth factor-enriched fraction is carried out at a pH of at least 3.5, more particularly at least 4, and not more than 4.5, the above-mentioned problems do not occur, so that upon the further treatment no growth factors are lost and the yield of growth factors is particularly high. Also, the treatment entails no modification, or less modification, of the growth factors. Filters, if any are used, and/or ion exchangers have been found not to silt up and therefore last longer. Surprisingly, the growth factors and the yield thereof hardly, if at all, sustain any adverse effects from the work under acid conditions.

Eligible as starting materials for the process according to the invention are milk and all milk derivatives that contain growth factors, such as cheese whey or casein whey. A preferred starting material is milk because milk contains considerable amounts of growth factors and is available in large amounts.

Preferably, the starting material is first subjected to a minimal heat treatment. This is advantageous because in such a heat treatment a considerable proportion of the bacteria naturally occurring in milk are killed. A minimal heat treatment is understood to mean a heating to 80° C. at a maximum, for not more than a few seconds.

Further, it is highly advantageous to strip the starting material of fat before subjecting it to the adsorption and elution steps. It has been found that after defatting, the column in which the cation exchanger is contained hardly becomes greased or clogged up during the step of adsorption to the cation exchanger. This prevents undue pressure build-up in the column and unfavorable shortening of the adsorption cycles.

It is preferred to carry out defatting by microfiltration, because this effects at the same time a reduction of the microbial contamination of the starting material. In this connection, microfiltration is understood to mean filtration with a filter having openings between 0.1 and 10 $\mu$m.

The cation exchanger to which the components from the milk or milk derivative are adsorbed can be any conventional cation exchanger in this field of the art. It is preferred to use a cation exchanger of a mean particle size in excess of 100 $\mu$m and of a sufficient mechanical strength to resist high pressures. This has as an advantage that the cation exchanger is resistant to high liquid loads, while the binding capacity is maintained, so that the large amounts of liquid that are required for an industrially applicable process can be processed in the desired short time. Examples of suitable cation exchangers are Toyo Pearl MD-P SP, SP-Toyo Pearl, SP-Sepharose and Sepharose Big Beads.

Preferably, the cation exchanger is pre-conditioned by buffering with a phosphate buffer of a pH value of 5.5–7.5. Then the milk or the milk derivative is passed through a column with the cation exchanger, for instance by pumping, whereby microcomponents adsorb from the starting material to the cation exchanger. The adsorption is preferably carried out at a temperature lower than 10° C. so as to keep any microbial growth to a minimum.

According to a preferred embodiment of the invention, the starting material is pumped at a high superficial velocity (more than 500 cm per hour) and at a high liquid load (100–600 bed volumes per hour) over a cation exchanger of a mean particle size of 100–300 $\mu$m, as described in the above-mentioned U.S. Pat. No. 5,596,082. According to this embodiment, a process is realized which is highly favorable from an economic point of view, having outstanding applicability on an industrial scale.

It is preferred after the adsorption step to cleanse the column with the cation exchanger of any residual milk product (starting material) by washing with a salt (NaCl) solution buffered at a pH between 5.5 and 7.5 and having a salt concentration of 0.2 molar or less.

After the adsorption of the starting material to the ion exchange resin, a fractionated elution is carried out. This means that elution is performed with different eluents in succession, so as to obtain a number of fractions having different microcomponent compositions.

Preferably, at least three elution steps are carried out with different salt solutions buffered at a pH between 5.5 and 7.5, preferably at a pH of about 6.5. By utilizing a progressively higher salt concentration, in succession fractions can be obtained which are enriched in different microcomponents coming from the milk or the milk derivative.

Elution with a solution of a low NaCl concentration, for instance of between 0.15 and 0.25 molar, yields a fraction containing substantially lactoperoxidase. By subsequent elution with a solution of a higher NaCl concentration, for instance of between 0.25 and 0.5 molar, the growth factor-enriched fraction is obtained, which further contains small amounts of lactoperoxidase and lactoferrin. By finally eluting with a salt solution containing a still higher concentration of molar NaCl, for instance of between 0.7 and 1.2, a fraction containing substantially lactoferrin is obtained.

The different fractions can be characterized through FPLC, 'fast protein liquid chromatography', with, for instance, a mono-S-column. If desired, this FPLC technique can also be used to further purify one or more of the obtained fractions on a preparative scale.

The fractions obtained, containing substantially lactoferrin and lactoperoxidase respectively, can be further treated according to conventional methods. These methods can comprise the steps of desalting, concentration, removing bacteria, and drying. Thus the process according to the invention can be combined in a highly advantageous manner with a process for recovering lactoferrin and lactoperoxidase from milk or a milk derivative on an industrial scale.

As has already been set out hereinabove, according to the invention it is of essential importance that the growth factor-enriched fraction obtained after the fractionated elution can be further treated at a mildly acid pH of not more than 4.5. Preferably, the growth factor-enriched fraction is further treated at a pH of at least 4, since thus a still higher yield of growth factors is achieved. The pH values mentioned can be achieved by acidifying the eluate with hydrochloric acid, or any other suitable acid that has no adverse effect on the growth factors. Preferably, food-approved acid is used.

One of the further treatments to which the growth factor-enriched fraction can be subjected is desalting. After the elution with the salt solutions, the fraction containing the desired growth factors will contain a considerable amount of salt, in particular NaCl. In a number of applications of the growth factors, the presence of these salts can be undesired. Desalting can be carried out utilizing electrodialysis or ultrafiltration. Ultrafiltration in this connection is understood to mean filtration over a membrane below 2.5 kDa. A great advantage of the invention is that there is no risk of the ultrafiltration membrane clogging up as a result of the presence of precipitates that can be formed in the growth factor-enriched fraction.

Another treatment that will typically be included in the further treatment is the further purification or concentration of the growth factor-enriched fraction. The further purification step preferably consists of a second chromatography step using a cation exchanger. In this step, the lactoperoxidase and lactoferrin present in the fraction are separated from the growth factors. Carrying out a second chromatography step is favorable because it does not entail any loss of growth factors, lactoferrin or lactoperoxidase, as often occurs by removing lactoferrin and lactoperoxidase, due to inactivation resulting from heating and separation.

It has been found that when a cation exchanger conditioned with a solution of an NaCl concentration of 0.15–0.25 molar is loaded with the growth factor-enriched fraction, the liquid which has passed through contains virtually all lactoperoxidase still present. By proceeding to elute in succession with NaCl solution of concentrations from 0.4–0.7 and 0.8–1.2 molar, two fractions are obtained. The first of those two contains virtually exclusively growth factors and the second contains reasonably pure lactoferrin.

A third treatment which can be a part of the further treatment of the growth factor-enriched fraction is removing the bacteria present therein and/or killing those bacteria. Preferably, the bacteria are removed by microfiltration, since this does not involve any product loss or product inactivation.

A fourth treatment to which the growth factor-enriched fraction can be subjected is drying for the purpose of promoting the keeping quality of the product obtained. Preferred methods of drying are spray-drying or freeze-drying.

If it is desired to separate the different growth factors present in the growth factor-enriched fraction obtained, the fraction can be subjected to a fifth treatment. Such a separation step can be performed, for instance, with preparative FPLC.

The above-mentioned five treatments that can be part of the further treatment of the growth factor-enriched fraction obtained according to the invention after fractionated elution, can be carried out in any suitable order. It will not be necessary or desired in all cases to carry out all five operations. In a given situation, the skilled person will be able to determine which operations are to be carried out in which order, depending on the application of the material obtained. In accordance with the invention, however, the above-mentioned problems of solids formation in the growth factor-enriched fraction do not occur in any of the five treatments.

Finally, the invention further relates to a growth factor or to a composition containing one or more growth factors, and to lactoperoxidase, lactoferrin or a composition containing lactoperoxidase or lactoferrin, obtainable utilizing the above-described processes.

The invention will presently be further elucidated in and by the following examples which are not be construed as being limitative.

EXAMPLE 1

An ion exchange column of a diameter of 1.6 meters was packed with 200 liters of coarse-grain (100–300 $\mu$m) cation exchanger (S-Sepharose Big Beads, obtainable from Pharmacia), yielding a bed height of 10 centimeters. The column was conditioned with a phosphate buffer (pH=6.5, 0.025 molar phosphate). For 3 hours, microfiltrated low-fat milk was pumped through this column at a rate of 100 bed volumes per hour, in total 60,000 liters.

Then the column was washed with 5 bed volumes of buffered (pH=6.5) 0.1 M NaCl solution. Then the microcomponents adsorbed to the column were successively eluted with:

a) 5 bed volumes of 0.2 M NaCl solution,
b) 5 bed volumes of 0.3 M NaCl solution,
c) 5 bed volumes of 1.0 M NaCl solution.

Eluates a) and c), containing substantially lactoperoxidase and lactoferrin respectively, were desalted by ultrafiltration at a pH of 6.5 and dried.

Eluate b), containing growth factors in addition to residues of lactoferrin and lactoperoxidase, was acidified to a pH of 4 with hydrochloric acid and then ultrafiltrated with a 2.5 kDa membrane (obtainable from Koch) until a conductivity of 2.5 mS was achieved (volume reduction 99%).

After microfiltration, neutralization to a pH of 6.5 occurred, followed by drying and analysis with FPLC. In the chromatogram obtained (FIG. 1) the peaks for lactoperoxidase (13.233 min) and lactoferrin (29.428 min) were clearly identifiable and peaks for the growth factors (14.782 to 19.011 min) could be distinguished.

EXAMPLE 2

Under identical conditions to those described in Example 1, a 0.3 M NaCl eluate was obtained from raw, low-fat milk.

This eluate was subjected to a second chromatography step, using a second column, of a diameter of 1.6 cm, packed with 40 ml of cation exchanger (S-Sepharose) and conditioned with 0.2 M NaCl solution with a pH of 6.5. The eluate was pumped through this column at a rate of 10 bed volumes per hour. The liquid which passed through contained residual lactoperoxidase, while the growth factors and the lactoferrin were adsorbed to the column.

Then elution took place with a 0.55 M NaCl solution (in total 5 bed volumes) and a 1 M NaCl solution in succession, the latter eluate thereby obtained containing lactoferrin. The fraction obtained by elution with 0.55 M NaCl solution was adjusted to a pH of 4 with hydrochloric acid, and ultrafiltrated to a conductivity of 2.5 mS.

Figure 2:
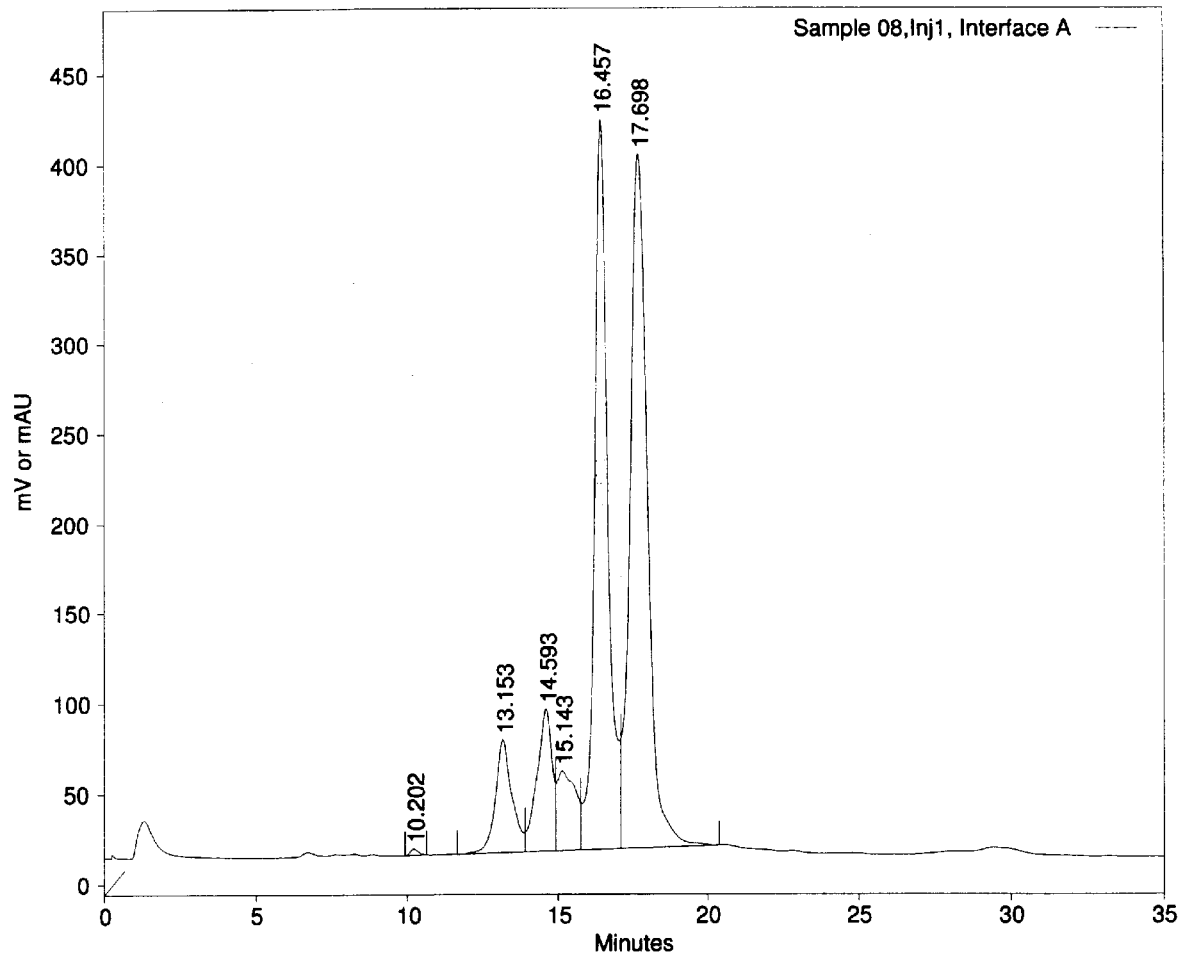

Using chromatographic identification with FPLC (FIG. 2) it was demonstrated that the product contained hardly any lactoferrin and/or lactoperoxidase anymore. Peaks of 10.202 to 17.698 min all identify growth factors.

The thus obtained product was separated using a mono-S cation exchanger column 5×5. The elution was carried out using two buffers:

Buffer A: 0.025 M $Na_2HPO_4$, pH 6.5
Buffer B: 0.025 M $Na_2HPO_4$, 2 M NaCl, pH 6.5.

The further conditions were: sample load 2.5 ml (6.2 mg); detection 220 nm, elution t=0 min: 0% buffer B, t=30 min 50% buffer B.

Five fractions were collected, which were further separated over a reversed phase column. The conditions were:

Column: Hipore 318 4.6×250 BioRad
Buffer A: 10 ml acetonitrile, 1000 ml milli Q water, 1 ml trifluoroacetic acid
Buffer B: 600 ml acetonitrile, 400 ml milli Q water, 1 ml trifluoroacetic acid
Detection 220 nm, sample load 100 $\mu$l, elution: t=0 min 0% buffer B; t=60 min 85% buffer B.

Figure 3:
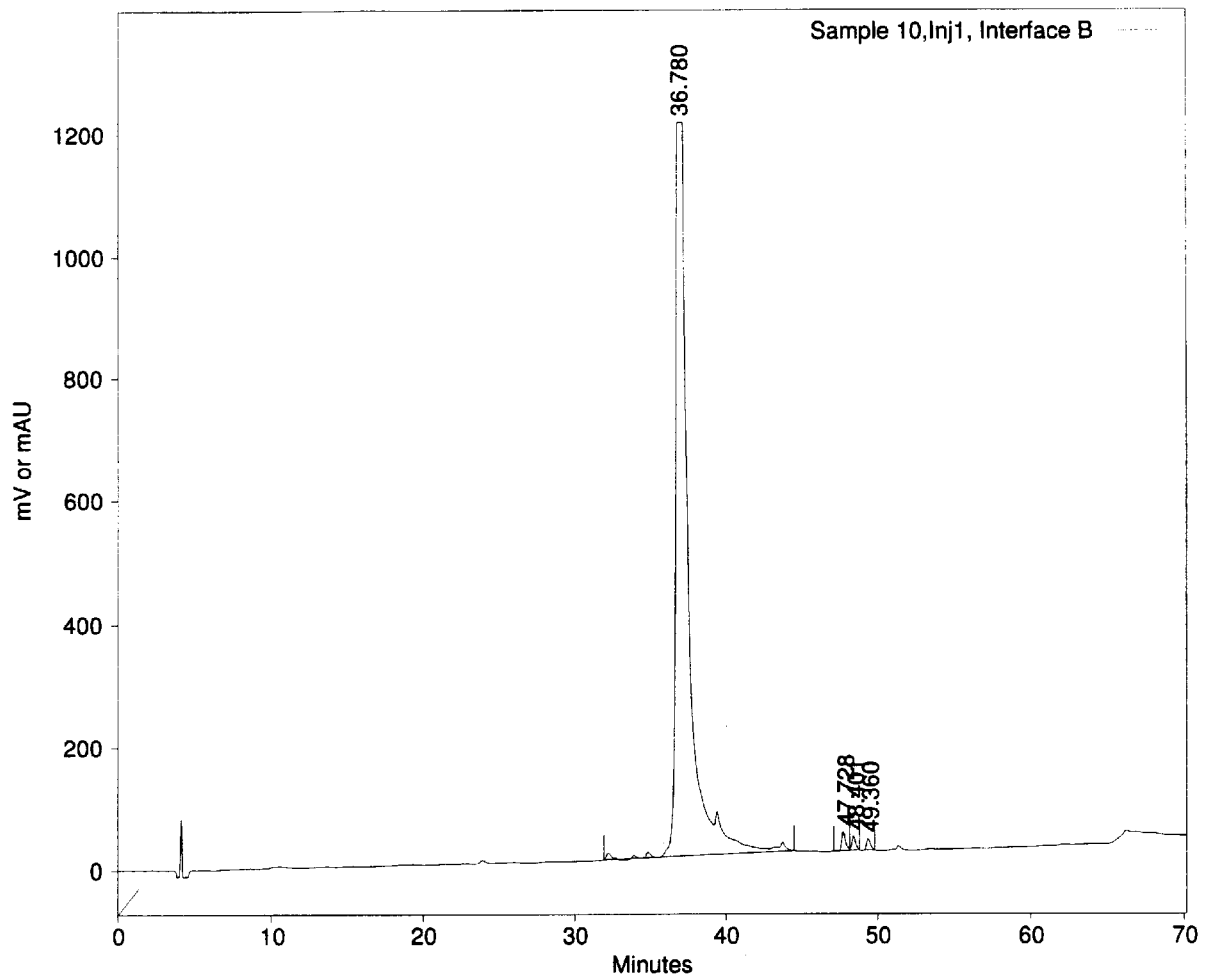
Figure 4:
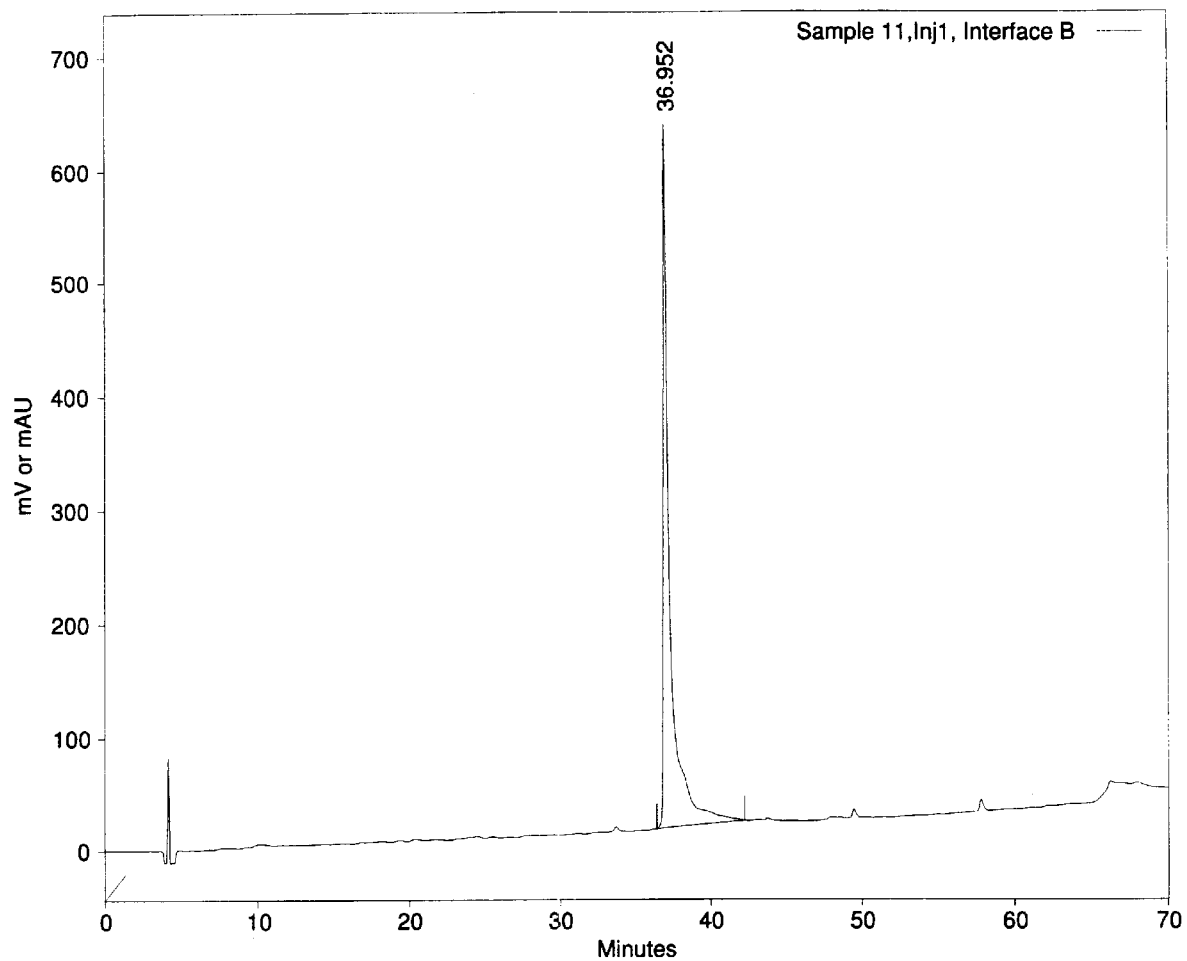

In FIGS. 3 and 4 the HPIC chromatograms of two of these separations are shown. FIG. 3 shows the chromatogram of a fraction—the angiogenin fraction, as appears from mass spectroscopy and N-terminal sequence analysis—which shows it to be virtually completely pure. FIG. 4 shows the chromatogram of another fraction which, as appears from mass spectroscopy and N-terminal sequence analysis, contains an angiogenin peptide.

We claim:

1. A process for recovering one or more growth factors from milk or a milk derivative, comprising adsorbing at least one growth factor from the milk or the milk derivative to a cation exchanger, followed by fractionated elution of the cation exchanger, whereby at least one fraction is obtained which is enriched in growth factors, followed by the further treatment of this fraction at a pH of at least 3.5 and not more than 4.5.

2. A process according to claim 1, wherein the further treatment of said fraction occurs at a pH of at least 4.

3. A process according to claim 1, wherein said fraction is further treated by desalting or concentration.

4. A process according to claim 3, wherein desalting occurs by ultrafiltration or by electrodialysis.

5. A process according to claim 3, wherein concentration occurs by again adsorbing to a cation exchanger and performing fractionated elution.

6. A process according to claim 1, wherein the milk or the milk derivative is defatted before the adsorption to the cation exchanger occurs.

7. A process according to claim 6, wherein the milk or the milk derivative is defatted utilizing microfiltration.

8. A process according to claim 7, wherein the milk or the milk derivative has previously undergone a minimal heat treatment.

9. A process according to claim 5, wherein the adsorption of at least one growth factor to a cation exchanger is carried out by passing the milk or the milk derivative at a high superficial velocity and a high liquid load through a column packed with the cation exchanger.

10. A process according to claim 5, wherein prior to the fraction which is enriched in growth factors, at least one fraction is recovered which is enriched in lactoperoxidase.

11. A process according to claim 10, wherein following the fraction which is enriched in growth factors, at least one fraction is recovered which is enriched in lactoferrin.

12. A process according to claim 10, wherein one or more of said fractions are further treated to form a lactoperoxidase or lactoferrin product.

13. A process according to claim 5, wherein further treatment occurs by killing or removing the bacteria present in the fraction.

14. A process according to claim 13, wherein the bacteria are removed utilizing microfiltration.

15. A process according to claim 14, wherein the fraction is further treated by spray-drying or freeze-drying.

16. A process according to claim 15, wherein the fraction which is enriched in growth factors is separated utilizing fast protein liquid chromatography techniques.

17. A process according to claim 16, wherein at least one fraction is recovered which is enriched in angiogenin or a peptide derived from angiogenin.

18. Growth factor or composition containing one or more growth factors, obtainable utilizing a process according to claim 17.

19. Lactoperoxidase or composition containing lactoperoxidase, obtainable utilizing a process according to claim 15.

20. Lactoferrin or composition containing lactoferrin, obtainable utilizing a process according to claim 15.

21. A process according to claim 1, wherein said fraction is further treated by desalting and concentration.

22. A process according to claim 10, wherein one or more of said fractions are further treated to form a lactoperoxidase and lactoferrin product.

23. A process according to claim 5, wherein further treatment occurs by killing and removing the bacteria present in the fraction.

24. A process according to claim 16, wherein at least one fraction is recovered which is enriched in angiogenin and a peptide derived from angiogenin.

* * * * *